United States Patent [19]

Guldhammer

[11] Patent Number: 5,780,502
[45] Date of Patent: Jul. 14, 1998

[54] USE OF 3,4-DIPHENYL CHROMANS FOR THE MANUFACTURE OF A PHARMACEUTICAL COMPOSITION FOR INHIBITING ONE OR MORE SYMPTOMS OF PREMENSTRUAL SYNDROME

[75] Inventor: Birgitte Hjort Guldhammer, Hillerød, Denmark

[73] Assignee: Novo Nordisk A/S, Bagsvaerd, Denmark

[21] Appl. No.: 889,670

[22] Filed: Jul. 8, 1997

Related U.S. Application Data

[60] Provisional application No. 60/031,245, Nov. 12, 1996.

[30] Foreign Application Priority Data

Jul. 12, 1996 [DK] Denmark .................. 0784/96

[51] Int. Cl.[6] .................. A61K 31/35; A61K 31/40
[52] U.S. Cl. .................. 514/456; 514/422
[58] Field of Search .................. 514/422, 456

[56] References Cited

U.S. PATENT DOCUMENTS

| | | | |
|---|---|---|---|
| 3,822,287 | 7/1974 | Bolger | 260/326.5 |
| 4,447,622 | 5/1984 | Salman et al. | 548/525 |
| 5,280,040 | 1/1994 | Labroo et al. | 514/422 |
| 5,453,442 | 9/1995 | Bryant et al. | 514/408 |

OTHER PUBLICATIONS

Joseph F. Mortola, M.D., "Pathophysiology and Treatment of Premenstrual Syndrome", 1995 Rapid Science Publishers ISSN 1068–3097, pp. 483–492.

*Primary Examiner*—Raymond Henley, III
*Attorney, Agent, or Firm*—Steve T. Zelson; Valeta Gregg

[57] ABSTRACT

The present invention provides novel uses of compounds of general formula I

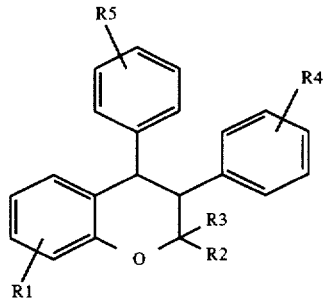

wherein $R^1$, $R^4$ and $R^5$ are individually hydrogen, hydroxy, halogen, trifluoromethyl, $C_{1-6}$ alkyl, $C_{1-6}$ alkoxy or (tertiary amino)( $C_{1-6}$ alkoxy); and $R^2$ and $R^3$ are individually hydrogen or $C_{1-6}$ alkyl, or a pharmaceutically acceptable salt thereof for the manufacture of a pharmaceutical composition for inhibiting one or more symptoms of premenstrual syndrome.

16 Claims, No Drawings

USE OF 3,4-DIPHENYL CHROMANS FOR THE MANUFACTURE OF A PHARMACEUTICAL COMPOSITION FOR INHIBITING ONE OR MORE SYMPTOMS OF PREMENSTRUAL SYNDROME

This application claims priority under 35 USC 119(E) of U.S. provisional application 60/031,245 filed Nov. 12, 1996.

FIELD OF THIS INVENTION

The present invention relates to the use of compounds of the general formula I for the inhibition of one or more symptoms of premenstrual syndrome. The present invention also embraces pharmaceutical compositions comprising these compounds and methods of using the compounds and their pharmaceutical compositions.

BACKGROUND OF THIS INVENTION

Premenstrual syndrome (PMS) is a common condition affecting a large proportion of women with normal functioning ovaries. The cause is still not known, but it seems to be related to the fluctuation of oestrogen and progesterone during the ovarian cycles. PMS is also referred to as late luteal phase syndrome (or late luteal phase dysphoric disorder).

The symptoms that occur can be both physical and psychological in nature. Irritability, snappiness and being on a "short fuse", depression and aggression are the most common reported psychological symptoms, but tension and anxiety are also frequent. Other psychological and behavioural symptoms which have been suggested to occur during the premenstrual phase and menstruation include, for example, decreased efficiency, insomnia, confusion, poorer judgement, difficulty in concentrating, crying, loneliness, restlessness, irritability, and mood swings. The effect of these symptoms can be compounded by physical symptoms which wary widely. The most common reported symptoms are tiredness, a feeling of abdominal bloating and breast swelling, and weight gain. Other symptoms which have been suggested to occur include, for example, dizziness, faintness, cold sweats, nausea, vomiting, hot flashes, muscle stiffness, headache, cramps, backache, general aches and pains, and water retention including, for example, weight gain, skin disorders, painful breasts, and swelling.

Numerous treatments have been suggested for alleviating or minimising symptoms of premenstrual syndrome. These include, for example, non-pharmaceutical therapy such as variation in total energy intake and consumption of protein, fat, carbohydrates, vitamin $B_6$ and E, as well as e.g. supplements of magnesium or calcium and Evening primrose oil containing gamolenic acid. Other treatments include non-hormonal therapy such as treatment with serotonin re-uptake inhibitors and hormonal therapy such as treatment with progesterone and progestogens, combined oral contraceptives, oestrogen replacement therapy, danazol and gonadotrophin hormone agonists. [See, e.g., Drug therapy in reproductive endocrinology, edited by Jean Ginsburg, Chapter 7 entitled "Premenstrual syndrome" by Abukhalil, I.E.H., et al: 107–115].

Although a variety of treatment options are available, a multitude of women continue to suffer from premenstrual syndrome on a monthly basis. Accordingly, the present invention provides methods for alleviating one or more menstrual symptoms in women associated with premenstrual syndrome, and compositions therefore.

Centchroman is a non-steroidal compound known to have antiestrogenic activity. It is in use in India as an oral contraceptive (see, for example, Salman et al., U.S. Patent Specification No. 4,447,622; Singh et al., Acta Endocrinal (Copenh) 126 (1992), 444–450; Grubb, Curr Opin Obstet Gynecol 3 (1991), 491–495; Sankaran et i., Contraception 9 (1974), 279–289; Indian Patent Specification No. 129187). Centchroman has also been investigated as an anti-cancer agent for treatment of advanced breast cancer (Misra et al., Int J Cancer 43 (1989), 781–783). Recently, centchroman as a racemate has been found as a potent cholesterol lowering pharmaceutical expressed by a significant decrease of the serum concentrations (S.D. Bain et al., J Min Bon Res 9 (1994), S 394).

U.S. Pat. No. 5,453,442 describes methods of lowering serum cholesterol and inhibiting smoother muscle cell proliferation in humans and inhibiting uterine fibroid disease and endometriosis in women by administering compounds of formula I as shown therein. Furthermore, U.S. Pat. No. 5,280,040 describes methods and pharmaceutical compositions for reducing bone loss using 3,4-diaryl chromans and their pharmaceutically acceptable salts. There is no disclosure in the patents of using the compounds to treat or alleviate premenstrual syndrome.

One object of the present invention is to provide compounds which can be used in alleviating one or more of the symptoms associated with premenstrual syndrome.

BRIEF DESCRIPTION OF THIS INVENTION

The present invention provides the use of compounds of the general formula I

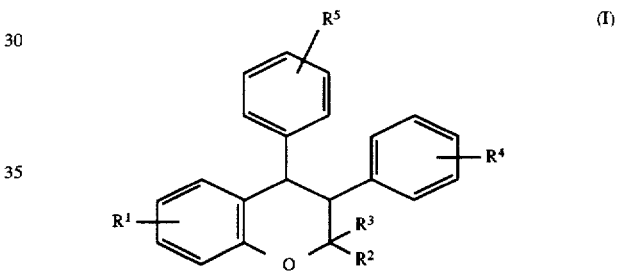

wherein $R^1$, $R^4$ and $R^5$ are individually hydrogen, hydroxy, halogen, trifluoromethyl, $C_{1-6}$ alkyl, $C_{1-6}$ alkoxy or (tertiary amino)( $C_{1-6}$ alkoxy); and $R^2$ and $R^3$ are individually hydrogen or $C_{1-6}$ alkyl, or a pharmaceutically acceptable salt thereof for the manufacture of a pharmaceutical composition for inhibiting one or more symptoms of premenstrual syndrome.

DETAILED DESCRIPTION OF THIS INVENTION

The present invention is based on the discovery that a group of 3,4-diarylchromans of formula I are useful for alleviating one or more of the symptoms associated with premenstrual syndrome. Thus, the present invention provides the use of a compound of the general formula I

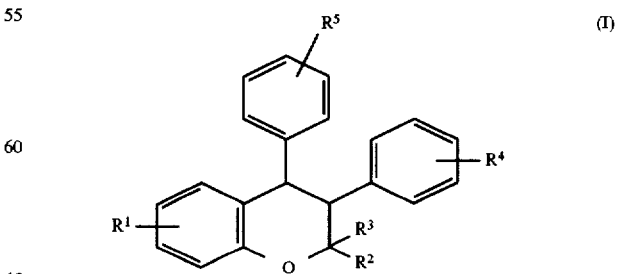

wherein $R^1$, $R^4$ and $R^5$ are individually hydrogen, hydroxy, halogen, trifluoromethyl, lower alkyl, lower alkoxy or (tertiary amino)(lower alkoxy); and $R^2$ and $R^3$ are individually hydrogen or lower alkyl, or as a pharmaceutically acceptable salt thereof in combination with a pharmaceutically acceptable carrier for the manufacture of a pharmaceutical composition for the treatment of premenstrual syndrome. Thus, the present invention provides a method of inhibiting one or more symptoms of premenstrual syndrome comprising administering to a subject in need of treatment an effective amount of a compound of formula I or a pharmaceutically acceptable salt thereof. The term "inhibit" is defined to include its generally accepted meaning which includes, for example, prophylactically treating a female human subject from incurring the symptoms of PMS, holding in check each symptom, alleviating one or more symptoms and/or treating existing symptoms. As such, the present method includes both medical treatment and/or prophylactic treatment, as appropriate.

Within the present invention, compounds of formula I as stated in claim 1 are used for inhibiting one or more symptoms of premenstrual syndrome in a patient. Within formula 1, $R^1$, $R^4$ and $R^5$ are individually hydrogen, hydroxy, halogen, trifluoromethyl, $C_{1-6}$ alkyl, $C_{1-6}$ alkoxy or (tertiary amino)($C_{1-6}$ alkoxy); and $R^2$ and $R^3$ are individually hydrogen or a $C_{1-6}$ alkyl. As used herein, the term "lower alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like. The term "lower alkoxy" includes straight and branched chain alkoxy radicals containing from 1 to 6 carbon atoms, such as methoxy, ethoxy, n-propoxy, isopropoxy, n-butoxy, tert-butoxy, n-20 amyloxy, sec-amyloxy, n-hexyloxy, 2-ethylbutoxy, 2,3-dimethylbutoxy and the like. "Halogen" includes chloro, fluoro, bromo and iodo. Herein, the term "(tertiary amino)(lower alkoxy)" is a lower alkoxy group which is substituted by a tertiary amino radical. The tertiary amino radical may be a N,N-dialkylamine such as a N,N-dimethylamino, N,N-diethylamino, N,N-dipropylamino and N,N-dibutylamino or a polymethyleneimine, e.g., piperidine, pyrrolidine, N-methylpiperazine or morpholine. Preferred compounds include those in which $R^1$ is lower alkoxy; $R^2$ and $R^3$ are lower alkyl, especially methyl; $R^4$ is hydrogen; and $R^5$ is (tertiary amino)(lower alkoxy) of the polymethyleneimine type. Within particularly preferred embodiments, $R^1$ is in the 7-position and is lower alkoxy, particularly methoxy; each of $R^2$ and $R^3$ is methyl, $R^4$ is hydrogen, and $R^5$ is in the 4-position and is a (tertiary amino)(lower alkoxy) radical such as 2-(pyrrolidin-1-yl)ethoxy. Preferred compounds include those in which $R^1$ is $C_{1-6}$ alkoxy; $R^2$ and $R^3$ are $C_{1-6}$ alkyl, especially methyl; $R^4$ is hydrogen; and $R^5$ is (tertiary amino)($C_{1-6}$ alkoxy) of the polymethyleneimine type. Within particularly preferred embodiments, $R^1$ is in the 7-position and is $C_{1-6}$ alkoxy, particularly methoxy; each of $R^2$ and $R^3$ is methyl, $R^4$ is hydrogen, and $R^5$ is in the 4-position and is a (tertiary amino)($C_{1-6}$ alkoxy) radical such as 2-(pyrrolidin-1-yl)ethoxy with formula 11

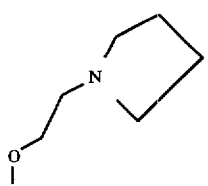

(II)

To be included by this invention are all pharmaceutically acceptable salts of the mentioned compounds of formula 1.

It is preferred to use the compounds of formula I in the transconfiguration. These compounds may be used as racemic mixtures, or the isolated d- or l- enantiomers may be used. The trans-l-enantiomers are more preferred.

A particularly preferred compound for use within the present invention is centchroman having the formula IV

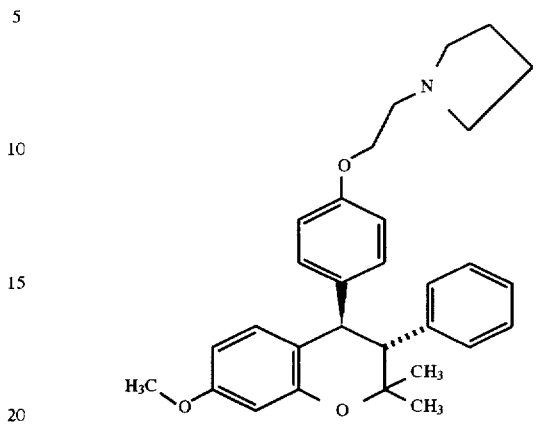

as stated in claim 11.

Although only one enantiomer is shown, it will be understood that the formula IV is used herein to designate the transconfiguration of the 3- and 4-phenyl groups and that both the d- and l-enantiomers, as well as the racemic mixture, are included. 3,4-diarylchromans are prepared according to known methods, such as those disclosed in U.S. Patent Specification No. 3,340,276 to Carney Me al., U.S. Patent Specification No. 3,822,287 to Bolger, and Ray B al., J Med Chem 19 (1976), 276–279, the contents of which are incorporated herein by reference. Conversion of the cis isomer to the trans configuration by means of an organometallic base-catalyzed rearrangement is disclosed in U.S. Patent Specification No. 3,822,287. The optically active d- and l-enantiomers may be prepared as disclosed by Salman et al. in U.S. Patent Specification No. 4,447,622 (incorporated herein by reference) by forming an optically active acid salt which is subjected to alkaline hydrolysis to produce the desired enantiomer. If $R^2$ is different from $R^3$ and $R^4$ is different from R5, the general formula I covers 8 optical isomers.

Within the present invention, 3,4-diarylchromans of formula I may be prepared in the form of pharmaceutically acceptable salts, especially acid-addition salts, including salts of organic acids and mineral acids. Examples of such salts include salts of organic acids such as formic acid, fumaric acid, maleic acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. A preferable salt is the hydrogen fumarate salt.

3,4-diarylchromans of formula I and their salts are useful within human and veterinary medicine, for example, in the treatment of patients suffering from premenstrual syndrome. For use within the present invention, 3,4-diarylchromans of formula I and their pharmaceutically acceptable salts are formulated with a pharmaceutically acceptable carrier to - provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in Remington's Pharmaceutical Sciences, Gennaro, ed., Mack Publishing Co., Easton, Pa, 1990.

The present invention further provides a pharmaceutical composition for alleviating one or more of the symptoms of premenstrual syndrome comprising a compound of formula I and at least one pharmaceutical agent selected from the group consisting of an analgesic, a diuretic, and an antihistamine, in combination with a pharmaceutically acceptable carrier, diluent or excipient.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered one or more times per day or week. An effective amount of such a pharmaceutical composition is the amount that provides a clinically significant effect against premenstrual syndrome. Such amounts will depend, in part, on the particular condition to be treated, age, weight, and general health of the patient, and other factors evident to those skilled in the art. A typical daily dose will contain a non-toxic dosage range of from about 0.001 to about 75 mg/kg patient per day of a compound of the present invention, preferably in a range from about 0.01 to 75, more preferably in the range from about 0.01 to 50 mg/kg patient per day.

The pharmaceutical compositions containing a compound of formula I may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., J Pharm Sci 73 (1964), 1294–1297, 1984; U.S. Patent Specification No. 4,489,056; and U.S. Patent Specification No. 4,210,644, which are incorporated herein by reference.

The following examples are offered by way of illustration, not limitation.

Examples of preferred compounds of formula I are centchroman as a racemic mixture and as isolated l-centchroman and d-centchroman enantiomers. Furthermore, 3,4-transdimethyl-3-phenyl-4-|4-(2-(pyrrolidin-1-yl)ethoxy)phenyl-7-hydroxychroman is a preferred compound. The more preferred compound is isolated l-centchroman (1-3,4-trans-2,2-imethyl-3-phenyl-4-|4-(2-pyrrolidin-1 -yl)ethoxy)phenyl|-7-methoxychroman).

Examples of pharmaceutically acceptable acid addition salts are salts with non-toxic acids, either inorganic acids such as hydrochloric acid, sulphuric acid and phosphoric acid, or organic acids such as formic acid, fumaric acid, acetic acid, propionic acid, succinic acid, gluconic acid, lactic acid, citric acid, ascorbic acid, benzoic acid, embonic acid, methaesulphonic acid and malonic acid.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLE

A clinical case-control study is performed in six to fifty women. The women are in good general health and have regular menstruation, but suffer from PMS as defined above. Symp- toms are reported by questionnaires. The women are divided into two groups, a test group which receives the active compound of this invention, and a control group which receives a placebo. Women in the test group receives between 1 and 500 mg of the test compound orally per day for one to six months. Regularly throughout the study symptoms are carefully recorded and the effects on the symptoms associated with PMS are compared both between the groups and for each patient also with the symptoms reported before treatment began. Effects on any of the symptoms of PMS of the test compound are considered as positive.

I claim:

1. A method of inhibiting one or more symptoms of premenstrual syndrome comprising administering to a patient in need thereof a clinically effective amount of a compound of formula I

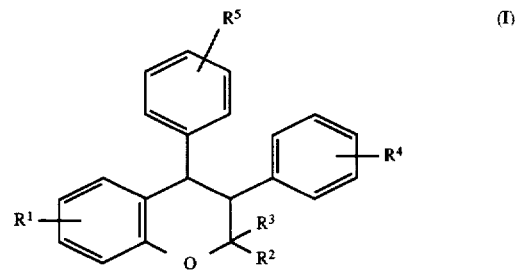

wherein $R^1$, $R^4$ and $R^5$ are individually hydrogen, hydroxy, halogen, trifluoromethyl, $C_{1-6}$ alkyl, $C_{1-6}$ alkoxy or (tertiary amino)($C_{1-6}$ alkoxy), and $R^2$ and $R^3$ are individually hydrogen or $C_{1-6}$ alkyl; or a pharmaceutically acceptable salt thereof.

2. The method of claim 1, wherein $R^1$ is $C_{1-6}$ alkoxy, $R^2$ and $R^3$ are $C_{1-6}$ alkyl, $R^4$ is hydrogen and $R^5$ is (tertiary amino) $C_{1-6}$ alkoxy.

3. The method of claim 1, wherein $R^1$ is methoxy.

4. The method of claim 1, wherein $R^2$ is methyl.

5. The method of claim 1, wherein $R^3$ is methyl.

6. The method of claim 1, wherein $R^4$ is hydrogen.

7. The method of claim 1, wherein $R^5$ is a group having the formula II

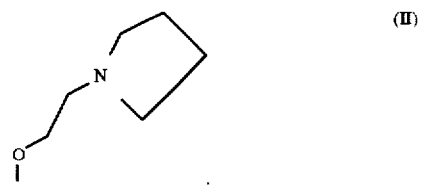

8. The method of claim 1, wherein said compound is an isolated d- or l- enantiomer.

9. The method of claim 1, wherein said compound has the formula III

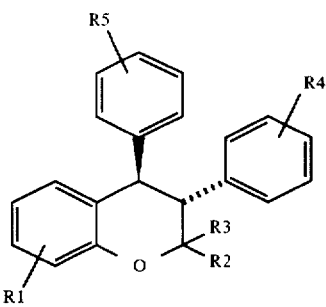

wherein $R^1$, $R^2$, $R^3$, $R^4$ and $R^5$ each are as defined in claim 1. defined in claim 1.

10. The method of claim 1, wherein said compound is 3,4-trans-2,2-dimethyl-3-phenyl-4|4-(2-(pyrrolidin-1-yl)ethoxy)phenyl-7-hydroxychroman.

11. The method of claim 8, wherein said compound is an isolated 1-enantiomer.

12. The method of claim 1, wherein said compound is centchroman 3,4-trans-2,2-dimethylin-1-yl)ethoxy)phenyl]-7-methoxychroman having the formula (IV)

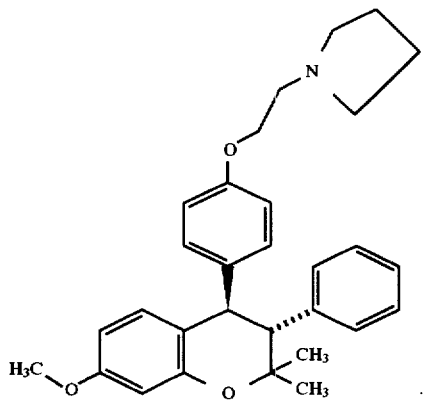

13. The method of claim 12, wherein said compound is an isolated 1-enantiomer of 3,4-trans-2,2-dimethyl-3-phenyl-4-|4-(2-pyrrolidin-1-yl)ethoxy)phenyl|-7-methoxychroman.

14. A method of inhibiting one or symptoms of premenstrual syndrome comprising admnistering to a patient in need thereof an effective amount of a pharmaceutical composition comprising a clinically effective amount of a compound of formula I

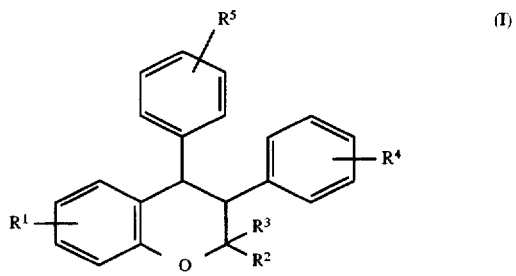

wherein $R^1$, $R^4$ and $R^5$ are individually hydrogen, hydroxy, halogen, trifluoromethyl, C1–6 alkyl C1–6 alkoxy or (tertiary amino)(C1–6 alkoxy), and $R^2$ and $R^3$ are individually hydrogen or C1–6 alkyl; or a pharmaceutically acceptable salt thereof, together with one or more pharmaceutically acceptable carriers or diluents.

15. The method of claim 14, wherein said compound is administered as a dose ranging from about 0.001 to 75 mg/kg patient per day.

16. The method of claim 14, wherein said composition is administered one or more times per day or week.

* * * * *